United States Patent [19]

Lindholm et al.

[11] Patent Number: 5,250,443
[45] Date of Patent: Oct. 5, 1993

[54] BIOLOGICAL DIAGNOSTIC ASSAY SYSTEM

[75] Inventors: Edward P. Lindholm, Brookline; Ernest J. Yamartino, Jr., Burlington, both of Mass.

[73] Assignee: PB Diagnostic Systems, Inc., Westwood, Mass.

[21] Appl. No.: 835,016

[22] Filed: Feb. 12, 1992

Related U.S. Application Data

[63] Continuation of Ser. No. 275,351, Nov. 23, 1988, abandoned.

[51] Int. Cl.$^5$ .............. G01N 33/549; G01N 21/00
[52] U.S. Cl. ............................ 436/529; 436/518; 436/535; 436/810; 436/546; 422/55; 422/57
[58] Field of Search ............ 436/529, 535, 810, 512, 436/518; 422/55, 56, 57

[56] References Cited

U.S. PATENT DOCUMENTS

| | | | |
|---|---|---|---|
| 3,836,433 | 9/1974 | Wirth et al. | 195/68 |
| 3,956,273 | 5/1976 | Guiseley | 260/209 R |
| 4,144,306 | 3/1979 | Figueras | 422/56 |
| 4,275,196 | 6/1981 | Shainoff | 536/115 |
| 4,312,727 | 1/1982 | Shainoff | 204/180 G |
| 4,806,311 | 2/1989 | Greenquist et al. | 422/56 |
| 4,824,870 | 4/1989 | Pemawansa et al. | 521/53 |
| 4,870,005 | 9/1989 | Akiyoshi et al. | 435/7 |
| 5,051,237 | 9/1991 | Grenner et al. | 422/56 |

FOREIGN PATENT DOCUMENTS 0232851  8/1987  European Pat. Off. .

OTHER PUBLICATIONS

Blot-Screening of Culture Fluid Immunoreactivities on Glyoxyl Agarose Films, Shainoff et al, Bio Techniques, vol. 4, No. 2, pp. 120-128.
Cascade Immunoelectrophoresis: Combined Electrophoretic And Solid-Phase Processing of Immunoreactive Protein By Zonal Immobilization, Shainoff et al, Journal of Immunological Methods, 42, (1981) pp. 229-241.
Electrophoretic Procedures for Zonal Immobilization of Proteins on Glyoxyl Agarose, Shainoff et al, CRC Handbook of Electrophoresis, vol. III, Lipoprotein Methodology and Human Studies, pp. 21-28.
Zonal Immobilization of Proteins, Shainoff, Biochemical and Biophysical Research Communications, vol. 95, No. 2 (1980) pp. 690-695.
Methods In Laboratory Investigation, Hoff et al, Laboratory Investigation, vol. 55, No. 3 (1986) pp. 377-386.

Primary Examiner—Esther L. Kepplinger
Assistant Examiner—Carol E. Bidwell
Attorney, Agent, or Firm—Gaetano D. Maccarone

[57] ABSTRACT

A multilayer diagnostic assay element wherein glyoxyl agarose, an aldehyde group - derivatized agarose, is utilized in one or more layers of the element. In a preferred embodiment the glyoxyl agarose is used to immobilize biological species such as a protein in a layer of the element.

9 Claims, 1 Drawing Sheet

BIOLOGICAL DIAGNOSTIC ASSAY SYSTEM

This application is a continuation of copending application Ser. No. 07/275,351 filed Nov. 23, 1988, now abandoned.

BACKGROUND OF THE INVENTION

The invention relates to multilayer diagnostic assay elements and, more particularly, to the use of materials therein which are suitable for immobilizing biological species such as proteins in a specific layer of the element.

Various types of diagnostic assay elements for the rapid analysis of analytes or metabolites in a biological fluid have been described. Generally, a sample of a biological fluid, e.g., plasma, serum, etc., is applied to the assay element and as a result of the interaction between an analyte or metabolite of interest and the reagent(s) present in the assay element a detectable change corresponding to the analyte or metabolite is brought about. The detectable change can be a color change which may be evaluated visually or read spectrophotometrically such as with a densitometer. In another scheme based on the presence of fluorescent - labeled biological species a fluorescent output signal is generated and read spectrofluorometrically.

Thin film multilayer assay elements which are suitable for carrying out immunometric assays have been described in the art. These thin film multilayer elements typically include a support carrying at least one reagent layer and a light blocking layer to permit the signal - generating species in one layer to be read out without interference from materials present in another layer. The elements may also include other layers to perform various functions such as, for example, a registration layer for holding a signal - generating species formed in or released from another layer.

In various of the assay methods it is required that a biological species, e.g., an antigen or an antibody be immobilized in a reagent layer and that such species remain in the particular layer throughout the assay. It is known to covalently bind proteinaceous materials such as antigens or antibodies to a matrix material such as agarose to form a reagent layer in such assay elements. However, this immobilization technique is not satisfactory in all instances. It is also known in immunometric assays carried out with classical wet chemistry methods to utilize proteins which are immobilized by being bound to polymeric bead materials. In these assays the biological species which do not interact with the immobilized proteins are typically removed from the reaction zone by means of a wash step. However, a wash step is typically not utilized with thin film multilayer assay elements because there is no provision for removal of the wash liquid which would include the unreacted reagents.

Therefore, there is a continuing need for new materials which can be used to provide various functions in multilayer assay elements.

It is therefore an object of the invention to provide a novel biological diagnostic assay system.

Another object of the invention is to provide multilayer biological diagnostic assay elements which include glyoxyl agarose, an aldehyde group derivatized agarose, in one or more layers.

A further object is to provide multilayer diagnostic assay elements for analytes having a molecular weight of about 5000 or less.

BRIEF SUMMARY OF THE INVENTION

These and other objects and advantages are accomplished in accordance with the invention by providing multilayer diagnostic assay elements wherein glyoxyl agarose an aldehyde group - derivatized polysaccharide, is utilized in one or more layers of the element. The glyoxyl agarose is useful for immobilizing biological species in a particular layer and retaining that species in the layer during the assay process. The material is also useful as a filter material, that is, it can prevent materials such as proteins, i.e., those having molecular weight of about 10,000 or above, from diffusing into or out of the layer while simultaneously allowing lower molecular weight materials, such as haptens or haptens labeled with a signal - generating dye, to diffuse into, out of or through the layer. The glyoxyl agarose may be used in more than one layer of the same diagnostic assay element. For example, the glyoxyl agarose may be used in a reagent layer to immobilize the reagent(s) located therein and also used in a filter layer in the same assay element.

The glyoxyl agarose may be used by itself as a matrix material for a reagent or filter layer or it may be used in conjunction with other polysaccharides such as underivatized agarose.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein.

DESCRIPTION OF THE PREFERRED EMBODIMENTS

Figure 1:
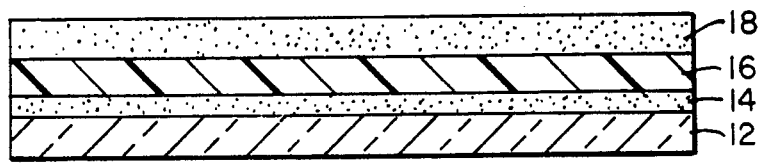
FIG. 1 is a partially schematic, cross-sectional view of a multilayer assay element according to the invention.

Glyoxyl agarose is described in U.S. Pat. No. 4,275,196 which also teaches that the material is useful for the zonal immobilization of proteins in electrophoretic techniques for the separation of complex proteins and subsequent analysis of the separated proteins. The patent does not suggest the use of glyoxyl agarose in the dry, thin film multilayer assay elements provided by applicants.

Glyoxyl agarose can be produced in a two step process. Initially, a suspension of commercial 4% agarose gel is treated with glycidol and a solution of 1M NaOH containing NaBH as an antioxidant. Subsequently, the resulting glyceryl agarose is cleaved by reaction with periodate to give glyoxyl agarose and formaldehyde. The glyoxyl agarose may have up to two aldehyde groups per biose unit of agarose.

The aldehyde-derivatized agarose undergoes a reversible reaction with a primary amine to form a Schiff base as illustrated by

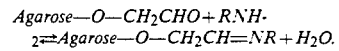

Agarose—O—CH$_2$CHO+RNH$_2 \rightleftharpoons$ Agarose—O—CH$_2$CH=NR+H$_2$O.

The equilibrium in this reaction shifts to the right with increasing pH. Thus, a protein such as an antibody can be covalently linked to the glyoxyl agarose through reaction of the amine groups of the protein with the aldehyde groups as illustrated previously.

The amount of aldehyde per unit weight of the derivatized agarose can vary depending upon the procedure used to prepare the derivatized material. The amount of available aldehyde per gram of derivatized material can be calculated by exploiting the reactivity of the aldehyde groups with p-nitrophenyl hydrazine to form hydrazones as illustrated by

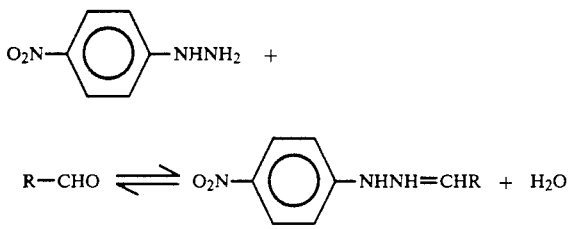

A circular sample (1" diameter) of a dried film of the glyoxyl agarose material carried by a polymeric support can be floated, coated side down, on the surface of 50 ml of the p-nitrophenyl hydrazine reagent at pH 4 in a sealed glass jar on an oscillating tray such that the films are gently agitated. After three hours the film samples are removed, washed well with water and allowed to dry in ambient conditions. The optical absorbance of the films at 390 nm is recorded and the meq of available aldehyde per gram of derivatized agarose is calculated, assuming a 1 cm pathlength and extinction coefficient ($\epsilon$) for hydrazone of 30,000.

A reagent layer according to the invention can be formed by initially preparing an aqueous solution of glyoxyl agarose (approximately 1% solids) by heating to boiling. Subsequently the solution is cooled to 50°-55° C. and a solution of the reagent(s) e.g., a proteinaceous material such as an antibody, and a buffer is added. The reaction to bind the antibody to the glyoxyl agarose requires a relatively high pH, about 8.5 or higher. The range of reactivity varies with the pH; increased binding occurs with increasing pH. The actual amount of binding is dependent upon the pH and the aldehyde content of the glyoxyl agarose. The material is coated as soon as is possible in order to avoid any undesirable denaturing of the antibodies at the elevated temperature. The layer is dried after coating during which the binding equilibrium is favored as the concentration of water is decreased. The reaction conditions also favor crosslinking reactions, for example via aldol condensation, of the glyoxyl agarose which provides a tight matrix structure. Upon standing the binding and cross-linking reactions continue to occur under the high pH conditions.

As noted previously the glyoxyl agarose may also be combined with other polysaccharides such as underivatized agarose. In a preferred embodiment of the invention an approximately 3:1 blend by weight of underivatized agarose:glyoxyl agarose is utilized in the thin film multilayer assay element. The blend is preferred because of the ease of handling during its preparation and subsequent processing. The blend can be prepared by blending a solution of glyoxyl agarose, typically less than 5% solids, at 50° C. with a solution of agarose with stirring at 50° C. and continuing to stir at 50° C. for several minutes. The blend, which preferably has from about 0.04 meq to about 0.20 mEq of available aldehyde per gram of total blend, can be used as prepared or it may be allowed to gel and subsequently heated at a future time when it is desired to incorporate the material into a thin film multilayer assay element.

Where another layer or layers will be coated over the glyoxyl agarose layer or the glyoxyl agarose layer is to be further treated in some manner such as by washing to reduce the pH of the dried layer it has been found that the initially formed layer should be allowed to cure for some period of time ranging from a few hours to a day or more.

Experiments have shown that the results which can be obtained according to the invention are dependent in part upon the aldehyde content of the matrix material (glyoxyl agarose or a blend of glyoxyl agarose with another polysaccharide) in the reagent, filter or other layer. The amount of aldehyde per unit weight of matrix material which will provide desired results in any specific assay element can vary over a wide range dependent upon variables such as the pH of the coating fluid from which the layer is formed and the particular buffer used in the coating fluid. As noted above, it is preferred to utilize as a matrix material an approximately 3:1 blend of underivatized agarose and glyoxyl agarose. A suitable blend having from about 0.04 mEq to about 0.20 mEq of available aldehyde per gram of blend can be prepared by blending one part of glyoxyl agarose having from about 0.16 mEq to about 0.8 mEq of available aldehyde per gram with three parts of agarose. Routine scoping tests may be used to ascertain the aldehyde content which will provide desired results in any layer of a specific multilayer assay element.

In the multilayer assay elements of the invention it may be necessary to coat another layer or layers over the glyoxyl agarose layer and depending upon the function of the layer(s) and the specific materials it may at times be necessary to coat one or more of these layers at a relatively low pH, i.e., below neutral pH. In these cases the Schiff base product should undergo the reverse reaction to the free amine (protein) and the polymeric aldehyde. However, even in these cases it has been found that the glyoxyl agarose layer continues to bind proteinaceous material efficiently. This property of coated glyoxyl agarose layers has been shown by experimental results. Although there is no intention to limit the invention to any theoretical mechanism, it is theorized that the glyoxyl agarose material forms a very tight matrix structure which binds reagent or other materials very efficiently under the typical assay conditions which generally include neutral pH.

Any suitable, biologically compatible alkaline buffer material which, when allowed to remain in the layer after formation thereof, does not interfere with the particular assay of interest can be used in the preparation of the glyoxyl agarose layers. As noted previously the pH of the coating fluid from which the glyoxyl agarose layer is coated can affect the equilibrium of the reaction of glyoxyl agarose with a primary amine to form a Schiff base and also crosslinking reactions for the glyoxyl agarose. Typical suitable buffers include Bicine, Bis-Tris-Propane, sodium carbonate and sodium borate. The choice of buffer appears to be dependent to some extent on the degree of aldehyde substitution of the glyoxyl agarose. For example, it appears that where the aldehyde substitution of the glyoxyl agarose is relatively less, better results are obtained with buffers having relatively high pKa or with inorganic buffers such as sodium carbonate. Generally for the same buffer material, higher pH provides better binding. However, different buffers used at the same pH may show differences in the results obtained.

FIG. 1 illustrates a particularly preferred assay element of the invention. The assay element 10 comprises a transparent support layer 12 carrying reagent layer 14, light blocking layer 16 and optional layer 18 which may be a reagent layer, a filter layer, e.g., for proteins, an anti-abrasion layer, etc. In one embodiment reagent layer 14 comprises an immunocomplex of an antibody complexed to a fluorescent-labeled antigen dispersed in a matrix of glyoxyl agarose or a blend of glyoxyl agarose with another matrix material such as agarose or the like. Reagent layer 14 is formed as previously described; in this instance the fluorescent-labeled antigens are incorporated in the coating composition along with the antibodies. Light blocking layer 16 comprises any suitable material such as, for example, iron oxide, titanium dioxide or the like dispersed in a binder such as agarose. Layer 18 is optional and may comprise an anti-abrasion layer of a material such as agarose where the reagent layer 14 includes the immunocomplex or it may include various materials such as a buffer, blocking and/or displacing agents, etc. Layer 18 can be omitted where the immunocomplex is present in reagent layer 14. In another embodiment the fluorescent-labeled antigen can be dispersed throughout layer 18 and layer 14 includes the immobilized antibody. The assay element 10 includes a coated layer or other means (not shown) for distributing the liquid sample uniformly across the surface of layer 18. Any suitable fluid distribution technique may be used including, for example, particulate layers, polymeric layers, fibrous layers, woven fabric layers and liquid transport systems which have been disclosed in the art as suitable for this purpose. Many such distribution materials for providing a uniform distribution of a sample fluid across the surface of an assay element are known in the art and therefore extensive discussion of such materials is not required here. A particularly preferred liquid transport system is that described in commonly assigned, copending application Ser. No. 210,732, filed Jun. 23, 1988 now U.S. Pat. No. 5,051,237. The distribution means, whether a layer of fibrous material, etc., or a liquid transport system should be relatively thick in comparison to reagent layer 14.

In practice the sample fluid is distributed across the assay element 10 and the fluid diffuses throughout layers 14, 16 and 18 as well as the distribution layer or system and an equilibrium is established. When present, an analyte, in this illustrative example an antigen (or hapten) of interest, will compete with the fluorescent - labeled antigen (the same antigen as the sample antigen or an analogue thereof) for the available binding sites on the antibodies immobilized in layer 14. In the instance where the fluorescent - labeled antigen is complexed initially to the antibody in layer 14, the former will be dissociated therefrom and replaced by the sample antigen in a ratio approximately equal to the relative amounts of sample antigen and fluorescent - labeled antigen. Where the fluorescent - labeled antigen is initially present in layer 18 it will be diffused into layer 14 along with the liquid sample and compete with the sample antigen for the binding sites on the immobilized antibody. Thus, in each embodiment, depending upon the amount of antigen present in the sample, some percentage of the fluorescent labeled antigens will bind to the immobilized antibodies which are not bound to the sample antigens. The remainder of the labeled antigens will be distributed throughout the remainder of the assay element. The amount of labeled antigen bound to the immobilized antibodies in reagent layer 14 at any time is inversely proportional to the amount of sample antigen. A quantitative determination of the sample antigen is obtained by irradiating the immobilized antibody layer through the transparent support layer 12 with appropriate excitation energy. Since the immobilized antibody layer 14 is very thin in comparison to the combined thickness of layers 16 and 18 together with that of the distribution layer or liquid transport system, i.e., typically a ratio of from about 1:20 to about 1:100, and because light blocking layer 16 prevents any of the excitation energy from entering layer 18 or anything above it, the optical readout system will measure the amount of labeled antigen which is bound to the immobilized antibodies and a very small percentage of the free labeled antigen which is distributed throughout the remainder of the assay element. As noted previously, the readout signal is inversely proportional to the amount of sample antigen, that is, the signal decreases as the amount of sample antigen increases.

It can be seen that the glyoxyl agarose layer 14 retains the antibodies immobilized therein during the assay whereas the sample antigens and the fluorescent - labeled antigens, both having a molecular weight smaller than that of the antibody, are able to diffuse into and out of reagent layer 14 in accordance with the equilibrium established in the element. Thus, the assay element shown in FIG. 1 is particularly well suited for the analysis of relatively small molecules, e.g., those having molecular weights of up to about 1500. Particularly preferred small molecules are drugs such as theophylline, phenytoin, carbamazepine, phenobarbital, etc.

Figure 2:
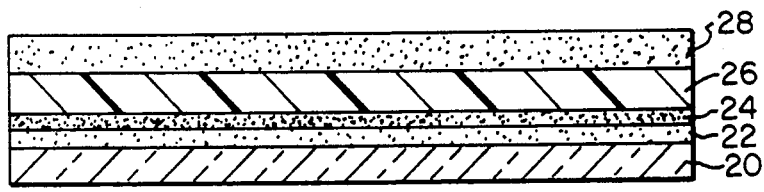
FIG. 2 is a partially schematic, cross-sectional view of another multilayer assay element according to the invention.

FIG. 2 illustrates another preferred assay element of the invention which comprises transparent support 20, reagent layer 22, filter layer 24, light blocking layer 26 and optional layer 28. In this embodiment, the reagent layer 22 can have a matrix of a polysaccharide such as agarose in which there is dispersed an immunocomplex made up of a fluorescent labeled antigen or analogue thereof and an antibody against that antigen. Filter layer 24 comprises glyoxyl agarose or a blend thereof as previously described. Light blocking layer 26 and optional layer 28 are as described in FIG. 1 with respect to layers 16 and 18 respectively. In practice, when the liquid sample is distributed across the assay element and diffuses throughout the element, the antibodies will diffuse through reagent layer 22 and become trapped by filter layer 24. This embodiment allows the reagent layer 22 to be coated at a lower pH which may be advantageous in the case of particular reagents.

Of course it will be understood that while the particular thin film multilayer elements illustrated in FIGS. 1 and 2 are preferred assay elements according to the invention, other such assay elements are provided. Generally, the thin film multilayer assay elements of the invention comprise one or more reagent layers, an optional light blocking layer and an optional filter layer wherein at least one reagent layer comprises a reagent immobilized in a matrix including glyoxyl agarose and/or another layer is formed of a matrix material including glyoxyl agarose. The thin film multilayer elements of the invention typically have a thickness of up to about 0.1 mm.

As noted previously U.S. Pat. No. 4,275,196 discloses glyoxyl agarose and further discloses that it is useful in the zonal immobilization of proteins of biological origin such as antigens, antibodies, etc. The patentee discloses the material for applications such as separation of complex proteins by electrophoresis and subsequent analysis of the isolated biological species. However, it is taught that the glyoxyl agarose must be reduced such as by contact with a reducing agent, e.g., cyanoborohydride ion, or it must shifted to a high pH ($\geq 10.0$). The present invention involves a dry multilayer assay element which provides permanent immobilization and therefore the pH of the layer may be lowered subsequently without the necessity of reducing the glyoxyl agarose. This characteristic of reagent layers formed according to the invention is illustrated by the experiments shown in Example II below.

The invention will now be described further in detail with respect to specific preferred embodiments by way of Examples, it being understood that these are intended to be illustrative only and the invention is not limited to the materials, conditions, process parameters, etc. recited therein.

EXAMPLE I

Glyoxyl agarose was prepared via periodate oxidation of glyceryl agarose. The product was found to have 0.533 mEq of available aldehyde per gram of derivatized material when analyzed by the hydrazone forming procedure described above herein.

A coating fluid was prepared at 50° C. by adding the following ingredients to 0.10 gm of agarose dissolved in 9.48 gms of distilled water: 300 $\mu$l of 0.25M sodium carbonate pH 9.0 buffer, 20 $\mu$m of 10% Tween 20 (a surfactant available from Rohm and Haas), and 200 $\mu$l of a glucose oxidase stock solution which contained 40 $\mu$m of 0.5M HEPES pH 7.5 buffer. 7.5 mg of glucose oxidase, and 7.5 mg of bovine serum albumin brought up to a total of 3.0 gms with distilled water. The coating fluid was applied to a subcoated polyethylene terephthalate base layer with a draw down rod and subsequently dried at room temperature. The dry layer had about 600 mg/m$^2$ of agarose and about 3 mg/m$^2$ of glucose oxidase.

A 4.82 cm$^2$ sample of the element was eluted with 5 ml of pH 7.0 phosphate buffer with gentle agitation for 30 minutes. A 1 ml aliquot of the buffer was removed and assayed for glucose oxidase activity by reacting it with glucose, horseradish peroxidase and o-phenylenediamine at pH 7.0 for 30 minutes. The absorbance of the oxidized o-phenylenediamine substrate at 492 nm was recorded.

Glucose oxidase layers were also formed with glyoxyl agarose and blends thereof with agarose as the matrix material. The results obtained are shown in Table I.

TABLE I

| Agarose: Glyoxyl Agarose (parts by weight) | Absorption @ 492 nm (O.D.) |
| --- | --- |
| 1:0 | 1.69 |
| 0:1 | 0.00 |
| 1:1 | 0.00 |
| 2:1 | 0.00 |
| 3:1 | 0.01 |
| 5:1 | 0.03 |

The results show that the agarose matrix allowed a large amount of the glucose oxidase to diffuse from the reagent layer whereas the glyoxyl agarose, by itself and in the blends including the 3:1 ratio, provided very effective immobilization of the glucose oxidase. It can also be seen that the 5:1 blend, while not as effective as the glyoxyl agarose layer and the layers made from the other blends, nevertheless was significantly more effective than the agarose layer in immobilizing the glucose oxidase.

EXAMPLE II

A control coating fluid was formed including 1% by weight agarose, 10 mM pH 7.0 HEPES buffer and I$^{125}$ labeled IgG antibodies in water. The coating fluid was applied to a subcoated polyethylene terephthalate base layer with a draw down rod and the antibody layer subsequently dried at room temperature. The dry layer had about 1000 mg/m$^2$ of agarose and about 15 mg/m$^2$ of I$^{125}$ labeled IgG antibodies.

Coating fluids were also prepared with 1% of a 3:1 blend of agarose and glyoxyl agarose (0.092 mEq of aldehyde per gram of blend) with pH 7.0 and 8.0 HEPES buffer (A & B), respectively, and also with pH 9.0 and 10.0 sodium carbonate buffer (C & D), respectively. The dry layers included about 1000 mg/m$^2$ of the agarose/glyoxyl agarose blend and about 15 mg/m$^2$ of the labeled antibodies.

The coated antibody layers were read initially with a Microstat Gamma Counter (Micromedic Systems, Inc.) and then immersed in 2 ml of pH 7.0 HEPES buffer for 30 minutes. The elements were read on the Gamma Counter after 10 minutes immersion time and after 30 minutes. The results are shown in Table II.

TABLE II

| ELEMENT | pH | BUFFER | RELATIVE SIGNAL 10 MIN. | 30 MIN. |
| --- | --- | --- | --- | --- |
| CONTROL | 7.0 | HEPES | 0.05 | 0.04 |
| A | 7.0 | HEPES | 0.92 | 0.52 |
| B | 8.0 | HEPES | 1.04 | 0.87 |
| C | 9.0 | SODIUM CARBONATE | 1.00 | 0.97 |
| D | 10.0 | SODIUM CARBONATE | 0.98 | 1.00 |

These data illustrate the effect of pH on immobilization with the different buffers. It can be seen that almost all of the I$^{125}$ labeled antibodies diffused out of the Control layer after 10 minutes. The antibody layers which included the glyoxyl agarose retained substantially all of the labeled antibodies after 10 minutes. Further, the antibody layers with the sodium carbonate buffer retained substantially all of the labeled antibodies even after 30 minutes at pH 9.0 and all the antibodies at pH 10.0. It is also apparent that the glyoxyl agarose layer including the HEPES buffer retained substantially more antibodies at pH 8.0 than at pH 7.0 after 30 minutes immersion.

EXAMPLE III

A control coating fluid was prepared at 50° C. by adding the followlng ingredients to 0.10 gm of agarose dissolved in 9.48 gms of distilled water: 400 $\mu$m of 0.25M Bis-Tris Propane pH 11.3 buffer, 20 $\mu$m of 10% Tween 20, and 200 $\mu$m of a glucose oxidase stock solution which contained 40 $\mu$m of 0.5 HEPES pH 7.5 buffer, 5.0 mg of glucose oxidase, and 5.0 mg of bovine serum albumin brought up to a total of 2.0 gms with distilled water. The composition was applied to a subcoated polyester terephthalate base layer with a draw down rod and the element dried at room temperature. The dry layer included about 1000 mg/m of agarose and about 300 mg/m² of buffer. The glucose oxidase layer was arranged in contact with 5 ml of a 0.1M sodium phosphate buffer solution (pH 7.0) and the combination arranged on a shaking table at gentle agitation. Aliquots of the buffer solution were removed at various intervals and assayed for GOD content.

Test layers were also formed with varying blends of agarose/glyoxyl agarose and varying aldehyde content. The test layers were also buffered by adding 400 μm of 0.25M sodium carbonate pH 9.0 buffer in place of the Bis-Tris Propane buffer above, resulting in a layer containing 90 mg/m of sodium carbonate. The data obtained are shown in Table III.

TABLE III

| ELEMENT | AGAROSE: GLY. AGAR. (PTS BY WT) | MEQ/GM ALDEHYDE CONTENT | Buffer | RELATIVE BATH ACTIVITY-GOD |
|---|---|---|---|---|
| CONTROL | 1:0 | — | BTP | 1.00 |
| A | 3:1 | 0.092 | " | 0.29 |
| B | 7:1 | 0.046 | " | 0.47 |
| C | 3:1 | 0.164 | " | 0.00 |
| D | 3:1 | 0.092 | SODIUM CARBONATE | 0.00 |
| E | 7:1 | 0.046 | SODIUM CARBONATE | 0.02 |
| F | 3:1 | 0.164 | SODIUM CARBONATE | 0.00 |

The glucose oxidase activities of the test elements are shown as relative values to the control which was normalized to 1.00. It can be seen that the glyoxyl agarose layers made with the sodium carbonate buffer were very effective in keeping the glucose oxidase immobilized in the reagent layer. It is also apparent that the two 3:1 blends with different aldehyde contents were equally effective in immobilizing the glucose oxidase. It can also be seen that the glyoxyl agarose layers made with the Bis-Tris-Propane buffer were increasingly effective as the aldehyde content of the matrix material increased.

EXAMPLE IV

An assay element according to the invention was prepared comprising a transparent subcoated polyethylene terephthalate support layer carrying in succession:

1. a reagent layer comprising about 500 mg/m² of a 3:1 agarose/glyoxyl agarose blend, about 21.5 mg/m² of sodium carbonate (pH 9.1) and about 10 mg/m² of a complex of theophylline antibodies and a fluorescent-labeled theophylline conjugate represented by the formula

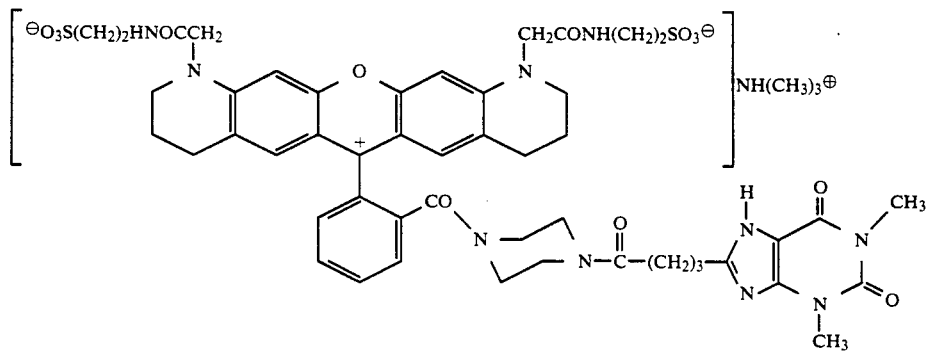

2. a light blocking layer comprising about 6000 mg/m² of iron oxide and about 15.1 mg/m² of 2'-morpholino ethane sulfonic acid (pH 5.7) in about 2000 mg/m² of agarose; and 3. a topcoat layer comprising about 2000 mg/m² of agarose.

An assay device was formed by placing the topcoat layer of the assay element in contact with the grooved surface of a sample application unit. The sample application unit, which is described in detail in commonly assigned copending application Ser. No. 133,071, filed Dec. 21, 1987 now U.S. Pat. No. 4,906,429, also included a filter element in fluid contact with the grooved surface. A sample having a known amount of theophylline was applied to the filter element. The device was then incubated at 37° C. for 30 minutes. Readings were taken every two minutes by irradiating the assay element through the base layer with 550 nm excitation energy from a xenon lamp. The fluorescent signal was read at 580 nm. The concentrations (μg/ml) of theophylline in the samples tested were: 0; 2.5; 5.0; 10.0; and 40.0, respectively.

The signal intensity for the samples decreased with successively increasing theophylline concentration thereby showing that the assay elements operated in the intended manner. Further, for each sample, after an initial period of time during which equilibrium was established (two minutes for the control and six minutes for the theophylline samples) the voltage signal remained substantially the same thereby showing that the antibodies remained immobilized in the reagent layer for the 30 minute period.

A standard curve based on the reading from the samples after six minutes incubation time was plotted. The readings were:

| Theophylline Concentration (μg/ml) | Signal (volts) |
|---|---|
| 0.0 | 1.242 |

| Theophylline Concentration ($\mu$g/ml) | Signal (volts) |
| --- | --- |
| 2.5 | 0.970 |
| 5.0 | 0.848 |
| 10.0 | 0.698 |
| 20.0 | 0.533 |
| 40.0 | 0.362 |

The standard curve was linear over the assay range (2.0-40 $\mu$g/ml) and had a relatively steep slope centered in the assay range.

EXAMPLE V

An assay element according to the invention was prepared comprising a transparent subcoated polyethylene terephthalate support layer carrying in succession:

1. a reagent layer comprising about 15 mg/m² of a complex of phenytoin antibodies and a fluorescent labeled phenytoin conjugate made up of a rhodamine dye shown in the theophylline conjugate illustrated in Example IV bound to phenytoin, and about 84 mg/m² of sodium carbonate (pH 9.0) dispersed in about 1000 mg/m² of a 3:1 blend of agarose/glyoxyl agarose;

2. a light blocking layer comprising about 6000 mg/m² of iron oxide and about 212 mg/m² of 2'-[N-morpholino]ethane sulfonic acid (pH 5.75) in about 2000 mg/m² of agarose; and 3. a topcoat layer comprising about 4000 mg/m² of a graft copolymer of agarose and polyacrylamide.

About 40 $\mu$m of plasma samples including known amounts of phenytoin (0, 2.0 and 50.6 $\mu$g/ml) were applied to discs (3.5 cm diameter) of the assay element by first applying the sample on a subcoated polyethylene terephthalate layer and then placing the assay element, topcoat layer down, on the liquid sample. The assay devices thus formed were placed in a laboratory instrument at 37° C. and the fluorescent signal read at two minute intervals by irradiating the assay element through the base layer with 550 nm excitation energy from a xenon lamp and collecting the fluorescent signal at 580 nm. The signal obtained from the assay element to which the control (0 $\mu$g/ml phenytoin) was added remained substantially the same over a thirty minute period thereby indicating that the antibodies did not diffuse from the reagent layer. Further, the signal decreased successively as the phenytoin concentration increased thereby showing that the assay element performed as intended.

EXAMPLE VI

An assay element according to the invention was prepared comprising a subcoated polyethylene terephthalate base layer carrying in succession:

1. a reagent layer including about 10 mg/m² of the complex of theophylline antibodies and the fluorescent labeled theophylline conjugate described in Example IV in about 500 mg/m² of agarose; and 2. a filter layer comprising 1000 mg/m² of a 3:1 blend of agarose/glyoxyl agarose.

Assay elements with this structure were also made wherein the filter layer was made from solutions buffered at different pH levels. A control assay element was made wherein the filter layer comprised about 1000 mg/m of agarose instead of the agarose/glyoxyl agarose blend.

A 3.3 cm² piece of each assay element was floated for 30 minutes, filter layer down, in about 2 ml of a pH 7.0 phosphate buffer. Subsequently, the assay elements were dried and the fluorescent emission signal measured. Similar experiments were carried out with pH 7.0 phosphate buffer which contained $10^{-3}$M theophylline. The data obtained are shown in Table IV:

TABLE IV

| AGAROSE: GLY. AGAR. (PTS. BY WT) | BUFFER | pH | SIGNAL NO THEO | SIGNAL 10-3M THEO |
| --- | --- | --- | --- | --- |
| 1:0 | HEPES | 7.0 | 0.03 | 0.02 |
| 3:1 | HEPES | 8.0 | 0.51 | 0.03 |
| 3:1 | Sodium Carbonate | 9.0 | 0.99 | 0.05 |
| 3:1 | Sodium Carbonate | 10.0 | 1.02 | 0.04 |

The data obtained from the assay elements floated in the buffer which did not contain any theophylline show that the filter layer comprised of agarose did not prevent the conjugate from diffusing out of the reagent layer whereas the filter layers which had the 3:1 agarose/glyoxyl agarose blend, particularly those which were buffered at pH 9.0 and 10.0 respectively, were effective in preventing the theophylline antibodies from diffusing. When the assay elements were contacted with the solutions containing $10^{-3}$M theophylline the competitive reaction occurred and very low signals were obtained. The $10^{-3}$M theophylline concentration was calculated to be sufficient to displace substantially all of the labeled theophylline conjugate originally present in the layers.

Although the invention has been described with respect to specific preferred embodiments it is not intended to be limited thereto but rather those skilled in the art will recognize that variations and modifications may be made therein which are within the spirit of the invention and the scope of the appended claims.

What is claimed is:

1. A multilayer diagnostic assay element comprising:
   a support layer;
   a reagent layer which comprises a reagent immobilized in a matrix material which includes glyoxyl agarose, wherein said glyoxyl agarose is not in the saturated amine form; and
   a light blocking layer.

2. The diagnostic assay element as defined in claim 1 wherein said matrix material comprises a mixture of said glyoxyl agarose and a different polysaccharide.

3. The diagnostic assay element as defined in claim 2 wherein said matrix material comprises a 3:1 mixture by weight of agarose and said glyoxyl agarose.

4. The diagnostic assay element as defined in claim 3 wherein said mixture has from about 0.04 mEq to about 0.20 mEq of available aldehyde per gram of total mixture weight.

5. The diagnostic assay element as defined in claim 4 wherein said reagent layer includes a protein immobilized in said matrix material.

6. The diagnostic assay element as defined in claim 5 wherein said protein is an antibody or an antibody fragment which specifically binds to the same analyte as said antibody.

7. The diagnostic assay element as defined in claim 6 wherein antibody or is specific for an analyte having a molecular weight of up to about 5000.

8. The diagnostic assay element as defined in claim 1 and further including a topcoat layer.

9. The diagnostic assay element as defined in claim 1 having a thickness of up to about 0.1 mm.

* * * * *